US009034275B2

(12) United States Patent (10) Patent No.: US 9,034,275 B2
Lee et al. (45) Date of Patent: May 19, 2015

(54) CHEMICAL SENSOR USING METAL NANO-PARTICLES AND METHOD FOR MANUFACTURING CHEMICAL SENSOR USING METAL NANO-PARTICLES

(71) Applicant: Electronics and Telecommunications Research, Daejeon (KR)

(72) Inventors: Myung Lae Lee, Daejeon (KR); Young Jun Kim, Daejeon (KR); Sung Hae Jung, Daejeon (KR); Ho Jun Ryu, Seoul (KR); Jong Moo Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 115 days.

(21) Appl. No.: 13/765,889

(22) Filed: Feb. 13, 2013

(65) Prior Publication Data

US 2013/0153113 A1 Jun. 20, 2013

Related U.S. Application Data

(62) Division of application No. 12/946,852, filed on Nov. 15, 2010, now Pat. No. 8,398,921.

(30) Foreign Application Priority Data

Dec. 18, 2009 (KR) .................. 10-2009-0127493
Jun. 25, 2010 (KR) .................. 10-2010-0060523

(51) Int. Cl.
*G01N 27/00* (2006.01)
*G01N 27/30* (2006.01)

(Continued)

(52) U.S. Cl.
CPC ............... *B32B 37/02* (2013.01); *Y10T 436/21* (2015.01);

(Continued)

(58) Field of Classification Search
None
See application file for complete search history.

(56) References Cited

U.S. PATENT DOCUMENTS 7,347,974 B1 3/2008 Snow et al.
2002/0132361 A1 9/2002 Vossmeyer et al.

FOREIGN PATENT DOCUMENTS

KR 10-2002-0046960 A 6/2002

OTHER PUBLICATIONS

Burkhard Raguse et al., "Gold Nanoparticle Chemiresistor Sensors: Direct Sensing of Organics in Aqueous Electrolyte Solution", Analytical Chemistry, Oct. 1, 2007, pp. 7333-7339, vol. 79, No. 19, American Chemical Society.

(Continued)

*Primary Examiner* — Neil N Turk (57) ABSTRACT

A chemical sensor using metal nano-particles and a method for manufacturing a chemical sensor using metal nano-particles are provided. The chemical sensor includes: metal nano-particles; single-ligand organic molecules (or a single molecule) that binds to the metal nano-particles by using a metal bonding functional group; a substrate bonding functional group formed at the metal nano-particles and the single-ligand organic molecules as bound to each other; a substrate; electrodes formed on the substrate and having an interdigitate (IDT) structure; and a substrate functional group formed on the substrate and positioned between the electrodes, wherein the substrate bonding functional group and the substrate functional group are covalently bonded.

4 Claims, 4 Drawing Sheets

(51) Int. Cl.
*B82Y 15/00* (2011.01)
*B82Y 40/00* (2011.01)
*B32B 37/02* (2006.01)
*B82Y 30/00* (2011.01)
*G01N 33/00* (2006.01)

(52) U.S. Cl.
CPC .......... *Y10T 29/49124* (2015.01); *Y10T 156/10* (2015.01); *Y10T 436/212* (2015.01); *B82Y 15/00* (2013.01); *B82Y 30/00* (2013.01); *B82Y 40/00* (2013.01); *G01N 33/0047* (2013.01)

(56) References Cited

OTHER PUBLICATIONS

H-L Zhang et al., "Vapour sensing using surface functionalized gold nanoparticles", Nanotechnology, May 23, 2002, pp. 439-444, vol. 13, IOP Publishing Ltd, UK.

CHEMICAL SENSOR USING METAL NANO-PARTICLES AND METHOD FOR MANUFACTURING CHEMICAL SENSOR USING METAL NANO-PARTICLES

CROSS-REFERENCE TO RELATED APPLICATIONS

This application is a divisional of U.S. patent application Ser. No. 12/946,852, filed on Nov. 15, 2010, which claims the priority of Korean Patent Application No. 10-2009-0127493 filed on Dec. 18, 2009 and No. 10-2010-0060523 filed on Jun. 25, 2010, in the Korean Intellectual Property Office, the disclosures of which are incorporated herein by reference.

BACKGROUND OF THE INVENTION

1. Field of the Invention

The present invention relates to a chemical sensor using metal nano-particles and a method for manufacturing a chemical sensor using metal nano-particles and, more particularly, to a chemical sensor using metal nano-particles having excellent detection characteristics and durability, and a method for manufacturing a chemical sensor using metal nano-particles.

2. Description of the Related Art

A typical chemical sensor is a metal oxide sensor, which performs sensing (or detection) at a high temperature (200 degrees Celsius to 400 degrees Celsius). Specifically, as metal oxide of a surface of the metal oxide sensor is activated at a high temperature, an oxidation-reduction reaction takes place between the metal oxide on the surface of the metal oxide sensor and target molecules to be sensed, thus performing sensing. Because the oxidation-reduction reaction irreversibly occurs, the activity of the surface degrades over time to end in a loss of the sensing function.

Thus, the service life of the metal oxide sensor is not long, and a correction function with respect to a change in sensing characteristics of the metal oxide sensor is performed even during the service life period. For all these drawbacks, metal oxide type sensors make up the majority of commercial sensors: The reason for this is because metal oxide has solidity or firmness in detection performance and chemical sensors have advanced in line with a great deal of commercialization efforts based on metal oxide playing a key role.

In order to overcome the inconvenience of high temperature detection, a sensor using a polymer detection film has been developed. This sensor includes a polymer as a detection film on an electrode. Detection is performed such that the polymer film absorbs a target material to be analyzed in the air and the mechanical or electrical characteristics of the polymer are affected by the amount of the absorbed target material, thus performing sensing.

A sufficient amount of sensing may take place at room temperature, so that sensing is performed at room temperature. A sensing reaction time relies on the dynamic equilibrium of the target molecules to be sensed on the surface of the polymer, and in general, the dynamic equilibrium on the surface of the polymer takes a long time.

There has been a case in which gold nano-particles surrounded with octanethiol were present in the form of a thin film on an electrode substrate, which was used as a chemical sensor. In this case, an excellent sensitivity for a level of 1 ppm of toluene was obtained, and a reaction time was a few seconds.

However, although the octanethiol gold nano-particle sensor exhibited excellent sensitivity for non-polar molecules, this was not the case for alcohol or water, both of which are polar sensing targets.

In another case, a layer of gold nano-particles surrounded with phenol was synthesized to implement a chemical sensor in the form of a thin film on an electrode substrate, which had good sensitivity for polar molecules. In particular, the chemical sensor is able to detect moisture even at a tens of ppm level.

However, even the lapse of scores of minutes at a 100 ppm degree did not reach saturation, indicating that the reaction was still going on. Namely, although the sensitivity for the polar molecules was excellent, the reaction time took too long.

In addition, the morphology of the sensor thin film of the chemical sensor using a polymer or metal nano-particles may change over time. In particular, a physical structure maintained by the sensor thin film may change according to an interaction between gas molecules and the sensor thin film, while reacting to various types of vapors, to result in a change in the sensing characteristics.

That is, unlike the metal oxide sensor, the chemical sensor does not involve a chemical irreversible reaction, so its sensing performance is not degraded over time, but the change in the physical structural characteristics of the sensor thin film as mentioned above is likely to degrade the reliability of the sensing operation of the chemical sensor.

SUMMARY OF THE INVENTION

An aspect of the present invention provides a chemical sensor using metal nano-particles having excellent sensing characteristics and durability.

Another aspect of the present invention provides a method for manufacturing a chemical sensor using metal nano-particles having excellent sensing characteristics and durability.

According to an aspect of the present invention, there is provided a chemical sensor including: metal nano-particles; single-ligand organic molecules (or only organic ligand molecules) that binds to the metal nano-particles by using a metal bonding functional group; a substrate bonding functional group formed at the metal nano-particles and the single-ligand organic molecules as bound to each other; a substrate; electrodes formed on the substrate and having an interdigitate (IDT) structure; and a substrate functional group formed on the substrate and positioned between the electrodes, wherein the substrate bonding functional group and the substrate functional group are covalently bonded.

The metal nano-particles and the single-ligand organic molecules as bound may be formed as a monolayer on the substrate.

The metal nano-particles may be gold (Au).

The single-ligand organic molecules may include a bottom and a body.

The bottom of the single-ligand organic molecules may be formed by one of an amine or a thiol.

The body of the single-ligand organic molecules may be formed by one of —$(CH_2)n$— and —$(CH_2CH_2O)n$—.

The body of the single-ligand organic molecules may have a structure of one of an aromatic ring and an aliphatic ring.

The substrate bonding functional group may include one of an amine, —COOH, and benzyl halogen.

The substrate may be made of one of silicon or glass.

The substrate functional group may include one of —OH, —$NH_2$, and —COOH.

According to another aspect of the present invention, there is provided a method for manufacturing a chemical sensor, including: binding metal nano-particles and single-ligand organic molecules by using a metal bonding functional group; forming a substrate bonding functional group at the metal nano-particles and the single-ligand organic molecules as bound; forming electrodes having an interdigitate (IDT) structure on a substrate; forming a substrate functional group between the electrodes formed on the substrate; and covalently bonding the substrate bonding functional group and the substrate functional group.

In binding the metal nano-particles and the single-ligand organic molecules by using the metal bonding functional group, a two-phase method may be used.

In forming the substrate bonding functional group at the metal nano-particles and the single-ligand organic molecules as bound, a ligand exchange reaction may be used.

In forming the electrodes having the IDT structure on the substrate, a lithography method may be used.

The single-ligand organic molecules that binds to the metal nano-particles by using the covalent bonding of the substrate bonding functional group and the substrate functional group may be formed as a monolayer on the substrate.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

The present invention may be modified variably and may have various embodiments, particular examples of which will be illustrated in drawings and described in detail.

However, it should be understood that the following exemplifying description of the invention is not intended to restrict the invention to specific forms of the present invention but rather the present invention is meant to cover all modifications, similarities and alternatives which are included in the spirit and scope of the present invention.

While terms such as "first" and "second," etc., may be used to describe various components, such components must not be understood as being limited to the above terms. The above terms are used only to distinguish one component from another. For example, a first component may be referred to as a second component without departing from the scope of rights of the present invention, and likewise a second component may be referred to as a first component. The term "and/or" encompasses both combinations of the plurality of related items disclosed and any item from among the plurality of related items disclosed.

When a component is mentioned as being "connected" to or "accessing" another component, this may mean that it is directly connected to or accessing the other component, but it is to be understood that another component may exist therebetween. On the other hand, when a component is mentioned as being "directly connected" to or "directly accessing" another component, it is to be understood that there are no other components in-between.

The terms used in the present application are merely used to describe particular embodiments, and are not intended to limit the present invention. An expression used in the singular encompasses the expression of the plural, unless it has a clearly different meaning in the context. In the present application, it is to be understood that terms such as "including" or "having," etc., are intended to indicate the existence of the features, numbers, operations, actions, components, parts, or combinations thereof disclosed in the specification, and are not intended to preclude the possibility that one or more other features, numbers, operations, actions, components, parts, or combinations thereof may exist or may be added.

Unless otherwise defined, all terms used herein, including technical or scientific terms, have the same meanings as those generally understood by those with ordinary knowledge in the field of art to which the present invention belongs. Such terms as those defined in a generally used dictionary are to be interpreted as having meanings equal to the contextual meanings in the relevant field of art, and are not to be interpreted as having ideal or excessively formal meanings unless clearly defined as having such in the present application.

Embodiments of the present invention will be described below in detail with reference to the accompanying drawings, where those components are rendered using the same reference number that are the same or are in correspondence, regardless of the figure number, and redundant explanations are omitted.

Figure 1:
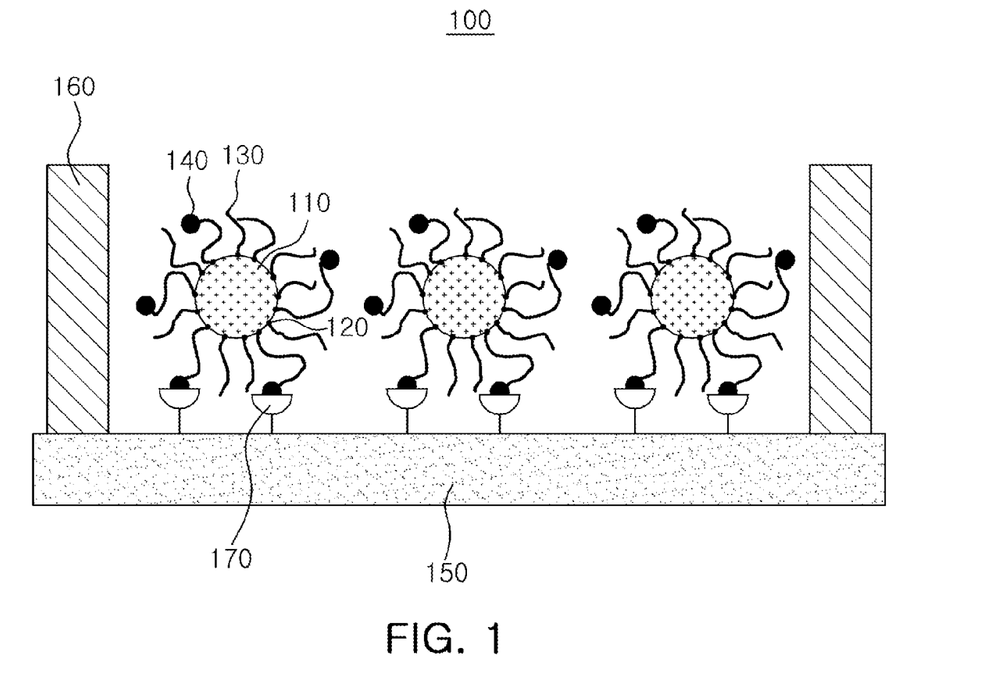
FIG. 1 is a view showing the structure of a chemical sensor using metal nano-particles according to an exemplary embodiment of the present invention.
Figure 2:
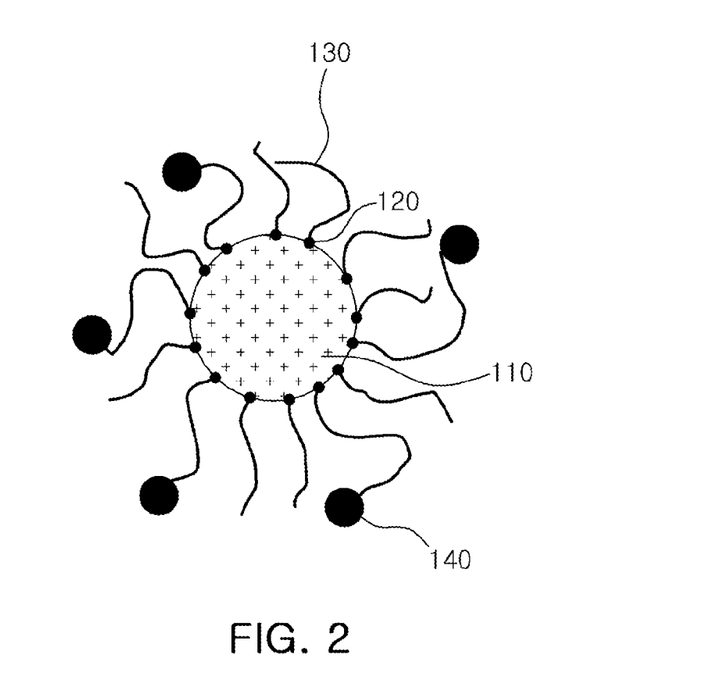
FIG. 2 is a view showing the structure of metal nano-particles and single-ligand organic molecules as bound in the chemical sensor using metal nano-particles according to an exemplary embodiment of the present invention.

FIG. 1 is a view showing the structure of a chemical sensor using metal nano-particles according to an exemplary embodiment of the present invention. FIG. 2 is a view showing the structure of metal nano-particles and single-ligand organic molecules as bound in the chemical sensor using metal nano-particles according to an exemplary embodiment of the present invention.

With reference to FIGS. 1 and 2, a chemical sensor 100 using metal nano-particles according to an exemplary embodiment of the present invention may include metal nano-particles 110, single-ligand organic molecules (or a single molecule) 130 that binds to the metal nano-particles 110 by using a metal bonding functional group 120, a substrate bonding functional group 140 formed at the metal nano-particles 110 and the single-ligand organic molecules 130 as bound to each other, a substrate 150, electrodes 160 formed on the substrate 150 and having an interdigitate (IDT) structure, and a substrate functional group 170 formed on the substrate 150 and positioned between the electrodes 160, wherein the substrate bonding functional group 140 and the substrate functional group 170 are covalently bonded.

In particular, in the chemical sensor 100 using metal nano-particles according to an exemplary embodiment of the present invention, the metal nano-particles and the single-ligand organic molecules as bound may be formed as a monolayer on the substrate.

Because the metal nano-particles and the single-ligand organic molecules as bound may be formed as a monolayer on the substrate, resistance can be adjusted by altering the size of the metal nano-particles and the size of the single-ligand organic molecules, and also, resistance can be adjusted by changing the space between the electrodes to a level of hundreds of nm to tens of um.

The metal nano-particles 110 is gold (Au). Silver (Ag) or platinum (Pt) may also be used as the metal nano-particles 110.

The single-ligand organic molecules 130 may bind to the metal nano-particles 110 by using the metal bonding functional group 120. The single-ligand organic molecules 130 may include a bottom and a body.

Here, the bottom of the single-ligand organic molecules 130 may be made of one of an amine or a thiol.

The body of the single-ligand organic molecules 130 may be made of one of —$(CH_2)n$— and —$(CH_2CH_2O)n$—. The body of the single-ligand organic molecules 130 may be formed to have a structure of one of an aromatic ring and an aliphatic ring.

The substrate bonding functional group 140 may be made of one of an amine, —COOH, and benzyl halogen. The substrate bonding functional group 140 may be used to be bound to the substrate 150. In particular, the substrate bonding functional group 140 may be covalently bonded with the substrate functional group 170 formed on the substrate 150.

The substrate 150 may be made of one of silicon and glass, and the substrate functional group 170 may be made of one of —OH, —$NH_2$, and —COOH.

The electrode 160 may have an interdigitate (IDT) structure and may have a comb-like shape.

Figure 3:
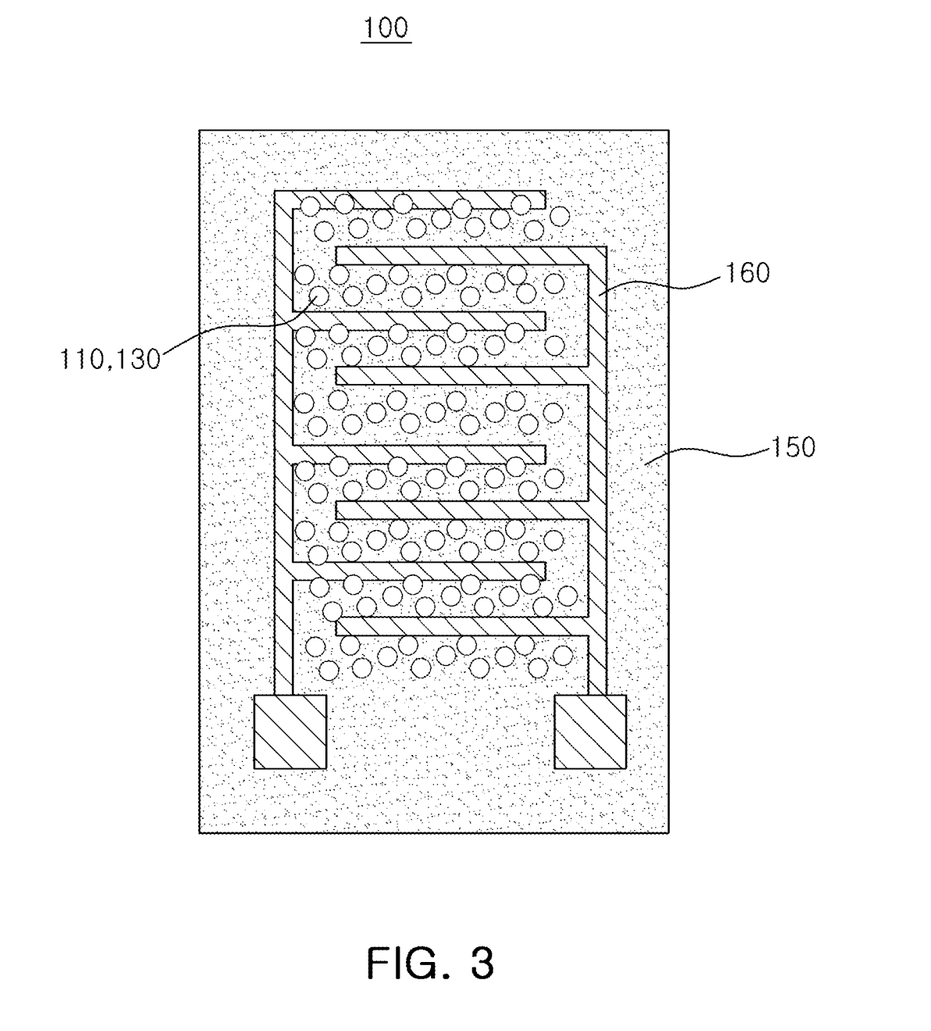
FIG. 3 is a plan view of the chemical sensor using metal nano-particles according to an exemplary embodiment of the present invention.

FIG. 3 is a plan view of the chemical sensor using metal nano-particles according to an exemplary embodiment of the present invention.

With reference to FIG. 3, the structure of the chemical sensor using metal nano-particles according to an exemplary embodiment of the present invention can be known. Namely, the chemical sensor 100 using metal nano-particles includes the substrate 150 and the IDT-structured electrodes 160 formed on the substrate 150. The combined body of the metal nano-particles and the single-ligand organic molecules may be bond to the substrate 150 through covalent bonding between the electrodes 160 formed in the comb-like shape.

When a gas desired to be detected is introduced in the structure, there occurs a change due to an interaction between the gas and the combined body of the metal nano-particles and the single-ligand organic molecules between the electrodes 160, and in this case the presence or absence of a particular gas as well as the density of the gas may be determined by detecting the change in the electrodes.

Figure 4:
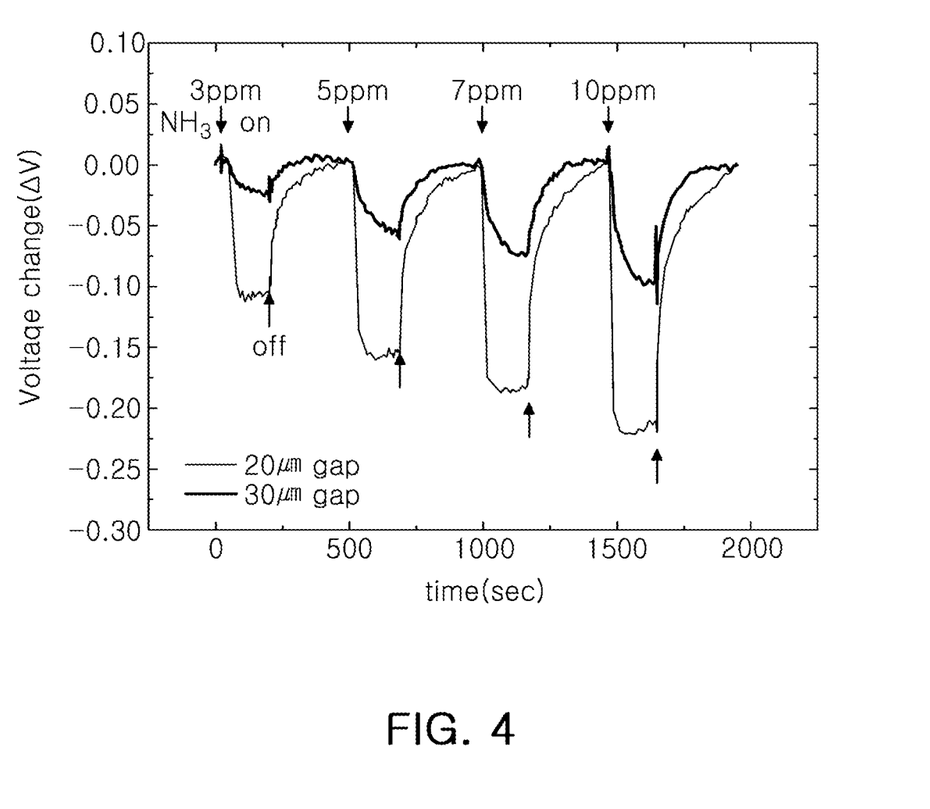
FIG. 4 is a graph for explaining the performance of the chemical sensor using metal nano-particles according to an exemplary embodiment of the present invention.

FIG. 4 is a graph for explaining the performance of the chemical sensor using metal nano-particles according to an exemplary embodiment of the present invention.

With reference to FIG. 4, when the chemical sensor using metal nano-particles according to an exemplary embodiment of the present invention performs sensing, it is noted that the potential of the electrode according to the density of a particular gas ($NH_3$) changes over a time axis (i.e., a horizontal axis).

Namely, it is noted that, as the density of the particular gas ($NH_3$) gradually increases, the variation of the potential of the electrode increases, and only a short period of time is required for detecting the particular gas ($NH_3$), although there is a slight difference in time.

As a result, it can be noted that the chemical sensor using metal nano-particles according to an exemplary embodiment of the present invention has excellent detection sensitivity and fast response time with respect to a particular gas, and because the substrate and the combined body of the metal nano-particles and the single-ligand organic molecules are bonded by covalent bonding, the chemical sensor using metal nano-particles according to an exemplary embodiment of the present invention has improved durability.

Figure 5:
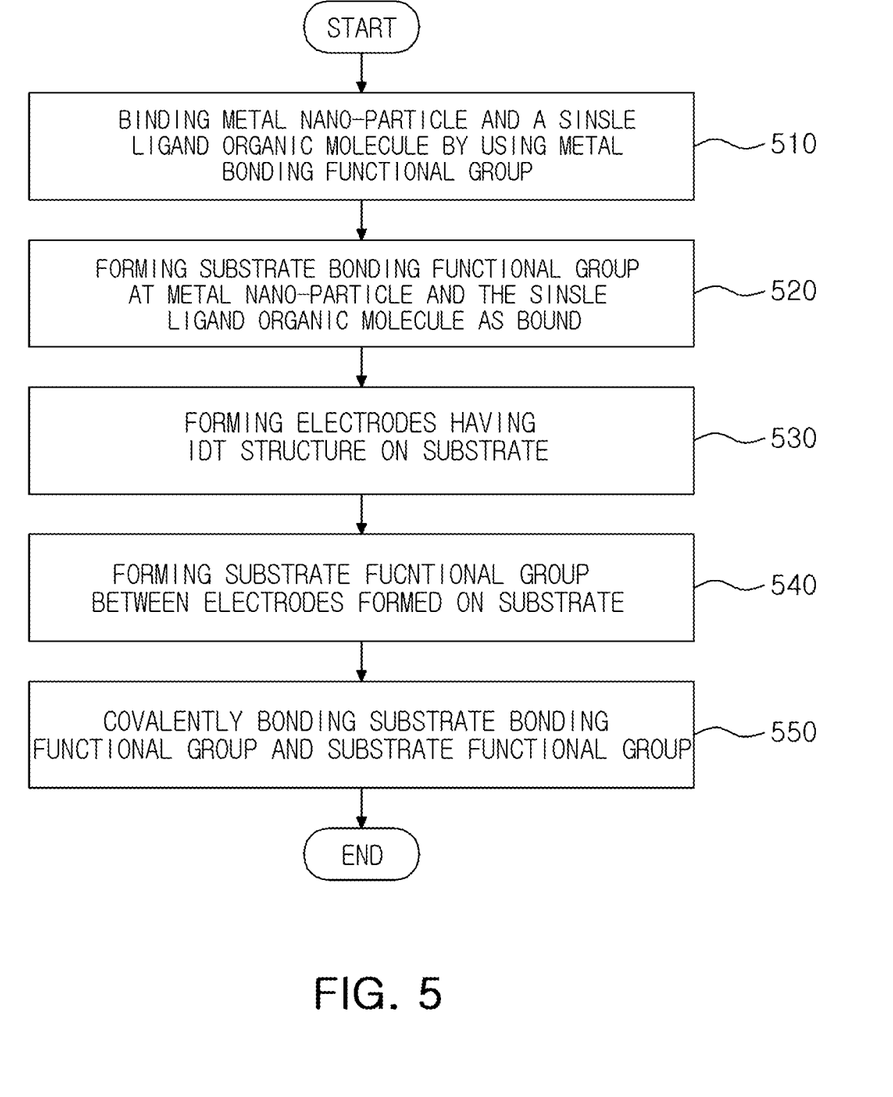
FIG. 5 is a flow chart illustrating the process of a method for manufacturing a chemical sensor using metal nano-particles according to an exemplary embodiment of the present invention.

FIG. 5 is a flow chart illustrating the process of a method for manufacturing a chemical sensor using metal nano-particles according to an exemplary embodiment of the present invention.

With reference to FIG. 5, a method for manufacturing a chemical sensor using metal nano-particles according to an exemplary embodiment of the present invention includes binding metal nano-particles and single-ligand organic molecules by using a metal bonding functional group (step 510), forming a substrate bonding functional group at the metal nano-particles and the single-ligand organic molecules as bound (step 520), forming electrodes having an interdigitate (IDT) structure on a substrate (step 530), forming a substrate functional group between the electrodes formed on the substrate (step 540), and covalently bonding the substrate bonding functional group and the substrate functional group (step 550).

First, in binding the metal nano-particles and the single-ligand organic molecules by using the metal bonding functional group (step 510), a two-phase method may be used.

Next, in forming the substrate bonding functional group at the metal nano-particles and the single-ligand organic molecules as bound (step 520), a ligand exchange reaction may be used.

Then, in forming the electrodes having the IDT structure on the substrate (step 530), a lithography method may be used.

Thereafter, in the covalent bonding between the substrate bonding functional group and the substrate functional group (step 550), the substrate and the combined body of the metal nano-particles and the single-ligand organic molecules may be bound, and the single-ligand organic molecules that binds to the metal nano-particles by using the covalent bonding of the substrate bonding functional group and the substrate functional group (step 550) may be formed as a monolayer on the substrate.

Preparation Example 1

Binding of Metal Nano-Particles and Single-Ligand Organic Molecules (in Case of Forming Bottom of Single-Ligand Organic Molecules with Thiol)

20.0 g of tetraoctylammonium bromide was dissolved in 800 ml of toluene, which was mixed with a solution obtained by dissolving $HAuCl_4$ (3.5 g, 8.9 mol) in 300 ml of water. The resultant mixture solution is then stirred for a few minutes.

4-methylbenzenethiol (1.08 g, 8.7 mol) and sodiumborohydride (3.8 g) dissolved in water (250 ml) were added to the mixture solution, which was then stirred for three hours to separate an organic layer.

The organic solvent was evaporated, suspended in ethanol, and put in a refrigerator to induce precipitation.

The precipitated product was cleansed with ethanol and then dried to obtain 4-methylbenzenethiol gold nano-particles (4-MB-AuNP).

Preparation Example 2

Binding of Metal Nano-Particles and Single-Ligand Organic Molecules (in Case of Forming Bottom of Single-Ligand Organic Molecules with Amine)

Tetraoctylammonium bromide was dissolved in toluene, which was then mixed with a solution obtained by dissolving $HAuCl_4$ in 300 ml of water. The resultant mixture solution was stirred for a few minutes.

Diaminobenzene and sodiumborohydride dissolved in water were added to the mixture solution, which was then stirred for three hours to separate an organic layer.

The organic solvent was evaporated, suspended in ethanol, and put in a refrigerator to induce precipitation.

The precipitated product was cleansed with ethanol and then dried to obtain diaminobenzene gold nano-particles.

Preparation Example 3

Binding of Metal Nano-Particles and Single-Ligand Organic Molecules (in Case of Forming Body of Single-Ligand Organic Molecules with —$(CH_2)n$-)

Tetraoctylammonium bromide was dissolved in toluene, which was then mixed with a solution obtained by dissolving $HAuCl_4$ in 300 ml of water. The resultant mixture solution was stirred for a few minutes.

n-alkylthiol and sodiumborohydride dissolved in water were added to the mixture solution, which was then stirred for three hours to separate an organic layer.

The organic solvent was evaporated, suspended in ethanol, and put in a refrigerator to induce precipitation.

The precipitated product was cleansed with ethanol and then dried to obtain n-alkylthiol gold nano-particles.

Preparation Example 4

Binding of Metal Nano-Particles and Single-Ligand Organic Molecules (in Case of Forming Body of Single-Ligand Organic Molecules with —$(CH_2CH_2O)n$-)

Tetraoctylammonium bromide was dissolved in toluene, which was then mixed with a solution obtained by dissolving $HAuCl_4$ in 300 ml of water. The resultant mixture solution was stirred for a few minutes.

$SH(CH_2CH_2O)n$-HS and sodiumborohydride dissolved in water were added to the mixture solution, which was then stirred for three hours to separate an organic layer.

The organic solvent was evaporated, suspended in ethanol, and put in a refrigerator to induce precipitation.

The precipitated product was cleansed with ethanol and then dried to obtain $SH(CH_2CH_2O)n$-HS gold nano-particles.

Preparation Example 5

Forming Substrate Bonding Functional Group at Metal Nano-Particles and Single-Ligand Organic Molecules as Bound 4-methylbenzenethiol gold nano-particles (4-MB-AuNP, 100 mg), a combined body of metal nano-particles and single-ligand organic molecules, was mixed with a large amount of 4-hydroxybenzenethiol (14 mg). The resultant mixture was dissolved in a solvent and then stirred for five days.

The final product was suspended in a solvent so as to be filtered, cleansed with a solvent, and the solvent was evaporated in a decompressed state to form a substrate bonding functional group at the metal nano-particles and the single-ligand organic molecules as bound.

Preparation Example 6

Forming Substrate Bonding Functional Group at Metal Nano-Particles and Single-Ligand Organic Molecules as Bound (in Case of Using Amine as Substrate Bonding Functional Group)

4-methylbenzenethiol gold nano-particles (4-MB-AuNP, 100 mg), a combined body of metal nano-particles and single-ligand organic molecules, was mixed with a large amount of 4-aminobenzenethiol. The resultant mixture was dissolved in a solvent and then stirred for five days.

The final product was suspended in a solvent so as to be filtered, cleansed with a solvent, and the solvent was evaporated in a decompressed state to form a substrate bonding functional group at the metal nano-particles and the single-ligand organic molecules as bound.

Preparation Example 7

Forming Substrate Bonding Functional Group at Metal Nano-Particles and Single-Ligand Organic Molecules as Bound (in Case of Using COOH as Substrate Bonding Functional Group)

4-methylbenzenethiol gold nano-particles (4-MB-AuNP, 100 mg), a combined body of metal nano-particles and single-ligand organic molecules, was mixed with a large amount of carboxylicbenzenethiol. The resultant mixture was dissolved in a solvent and then stirred for five days.

The final product was suspended in a solvent so as to be filtered, cleansed with a solvent, and the solvent was evaporated in a decompressed state to form a substrate bonding functional group at the metal nano-particles and the single-ligand organic molecules as bound.

Preparation Example 8

Forming Substrate Bonding Functional Group at Metal Nano-Particles and Single-Ligand Organic Molecules as Bound (in Case of Using Benzyl Halogen as Substrate Bonding Functional Group)

4-methylbenzenethiol gold nano-particles (4-MB-AuNP, 100 mg), a combined body of metal nano-particles and single-ligand organic molecules, was mixed with one of a large amount of bromobenzenethiol and chlorobenzenethiol. The resultant mixture was dissolved in a solvent and then stirred for five days.

The final product was suspended in a solvent so as to be filtered, cleansed with a solvent, and the solvent was evaporated in a decompressed state to form a substrate bonding functional group at the metal nano-particles and the single-ligand organic molecules as bound.

Preparation Example 9

Formation of Electrode Having Interdigitate (IDT) Structure on Substrate

The substrate 150 made of one of silicon or glass was cleansed, on which photoresist (PR) was spin-coated.

A mask with an IDT electrode arranged drawn thereon was aligned with the substrate by using a stepper or a contact aligner, exposed, and then developed to form a PR pattern.

Here, either an intaglio pattern or an embossed pattern may be used, and the PR in use may change according to circumstances.

A metal film was evaporated on the PR pattern-formed substrate by using one of E-beam and sputtering, and then the PR was removed to complete an IDT-formed substrate.

Preparation Example 10

Formation of Functional Group Between Electrodes Formed on Substrate (in Case of Using —OH as Substrate Functional Group Because an OH group exists on a glass substrate, the glass substrate was used as it is.

In the case of a silicon substrate, an oxide layer was evaporated with a thickness ranging from tens of nm to hundreds of nm on the surface of the silicon substrate to introduce an OH functional group.

Preparation Example 11

Formation of Functional Group Between Electrodes Formed on Substrate (in Case of Using —$NH_2$ as Substrate Functional Group One of the glass substrate and the silicon substrate with the oxide film deposited thereon was sequentially cleansed with deionized water, ethanol, THF, deionized (DI) water and then dried.

One of 2% of 3-aminopropyl trimethoxysilane and 3-aminopropyltriethoxysilane was prepared, the —OH substrate was deposited in this solution for four hours and then dried at 100 degrees Celsius.

Preparation Example 12

Formation of Functional Group Between Electrodes Formed on Substrate (in Case of Using —COOH as Substrate Functional Group A 10% solution of one of COOH—$C_6H_6$—COOH and COOH—$(CH)_4$—COOH was prepared.

DI water, THF, or ethanol was used as a solvent.

An amine substrate was deposited in the solution under an acid or a base catalyst to install a COOH group on the surface.

Preparation Example 13

Covalent Bonding of Substrate Bonding Functional Group and Substrate Functional Group Before placing gold nano-particles between electrodes on the manufactured substrate, the electrodes were put in a piranha solution ($H2SO4/H2O2=3:1$), sonicated for one minute, and then cleansed with methanol and acetone.

The gold nano-particles were dissolved in a solvent, and the substrate electrodes were then dip-coated to form covalent bonding of the substrate bonding functional group and the substrate functional group.

As set forth above, according to exemplary embodiments of the invention, a chemical sensor, which supplements the drawbacks of the existing metal nano-particles sensor while maintaining the advantages of the existing metal nano-particles sensor, can be provided.

Also, the chemical sensor can be simply fabricated, designed to have elaborate sensing characteristics, and fabricated to have a very small size.

In particular, the chemical sensor has the sensing characteristics of very excellent detection of polar and non-polar molecules, a fast response speed, and long-lasting detection performance and characteristics, thus acquiring excellent durability and reliability.

As a result, the chemical sensor having the three major properties of sensitivity, a response speed, and durability can be provided.

While the present invention has been shown and described in connection with the exemplary embodiments, it will be apparent to those skilled in the art that modifications and variations can be made without departing from the spirit and scope of the invention as defined by the appended claims.

What is claimed is:

1. A method for manufacturing a chemical sensor, the method comprising:
    binding metal nano-particles to a first end of single-ligand organic molecules through a metal bonding functional group;
    forming a substrate bonding functional group at a second end of the single-ligand organic molecules;
    forming electrodes having an interdigitate (IDT) structure on a substrate;
    forming a substrate functional group on an exposed surface of the substrate between the electrodes; and
    covalently bonding the substrate bonding functional group and the substrate functional group.

2. The method of claim 1, wherein a ligand exchange reaction is used to form the substrate bonding functional group.

3. The method of claim 1, wherein the electrodes are formed using lithography.

4. The method of claim 1, wherein the metal nano-particles are arranged as a monolayer on the substrate.

* * * * *